US00PP15546P2

(12) United States Plant Patent
Leue

(10) Patent No.: US PP15,546 P2
(45) Date of Patent: Feb. 8, 2005

(54) ***ANGELONIA* PLANT NAMED 'BALANGBEKE'**

(50) Latin Name: *Angelonia angustifolia*
Varietal Denomination: Balangbeke

(75) Inventor: Ellen F. Leue, DeKalb, IL (US)

(73) Assignee: Ball Horticultural Company, West Chicago, IL (US)

( * ) Notice: Subject to any disclaimer, the term of this patent is extended or adjusted under 35 U.S.C. 154(b) by 18 days.

(21) Appl. No.: 10/741,640

(22) Filed: Dec. 19, 2003

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—Wood, Phillips, Katz, Clark & Mortimer

(57) ABSTRACT

A new and distinct cultivar of *Angelonia* plant named 'Balangbeke' characterized by its violet-blue-colored flowers, medium green-colored foliage, and semi-prostrate to trailing, well branched growth habit.

1 Drawing Sheet

Latin name of genus and species of plant claimed: *Angelonia angustifolia.*
Variety denomination: 'Balangbeke'.

BACKGROUND OF THE INVENTION

The present invention relates to a new and distinct cultivar of *Angelonia* plant botanically known as *Angelonia augustifolia* and hereinafter referred to by the cultivar name 'Balangbeke'.

The new cultivar was developed by the inventor in a controlled breeding program during June 2000, at Elburn, Ill. The objective of the breeding program was the development of *Angelonia* cultivars with freely branching and vigorous growth habits, unique flower colors and continuous flowering.

The female parent of the new cultivar was the proprietary *Angelonia augustifolia* selection designated '190LV' (not patented) characterized by its deep lavender blue-colored flowers, medium green-colored foliage, and spreading growth habit. The male parent of the new cultivar was the proprietary *Angelonia augustifolia* selection designated '225E' (not patented) characterized by its deep lavender-colored flowers, medium green-colored foliage and well branched semi-upright growth habit. The new cultivar was discovered and selected as a single flowering plant among the progeny of the above cross-pollination by the inventor during September 2001 in a controlled environment at Elburn, Ill. and was initially designated '165-4'.

Asexual reproduction of the new cultivar by terminal stem cuttings since February 2001 at Elburn and West Chicago, Ill. has demonstrated that the new cultivar reproduces true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length.

It was repeatedly found that the cultivar of the present invention:

1. Exhibits purple-colored flowers,
2. Forms medium green-colored foliage, and
3. Exhibits a semi-prostrate to trailing, well branched growth habit.

Plants of the new cultivar differ from plants of the female parent primarily in growth habit and from plants of the male parent primarily in flower color.

Of the many *Angelonia* cultivars known to the inventor, the most similar to 'Balangbeke' is the *Angelonia* cultivar Balangimpu (U.S. Plant Pat. No. 13,921). However, in side-by-side comparisons, plants of the new cultivar differ from plants of 'Balangimpu' primarily in flower color.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balangbeke'. The plants were grown in 10 cm pots for 10 weeks in a greenhouse at West Chicago, Ill.

DETAILED BOTANICAL DESCRIPTION

Figure 1:
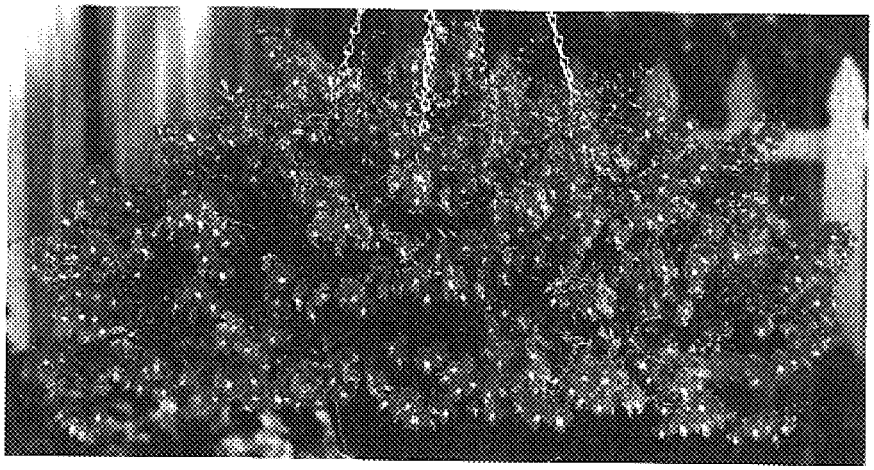
FIG. 1 illustrates a side view of the overall growth and flowering habit of 'Balangbeke'.
Figure 2:
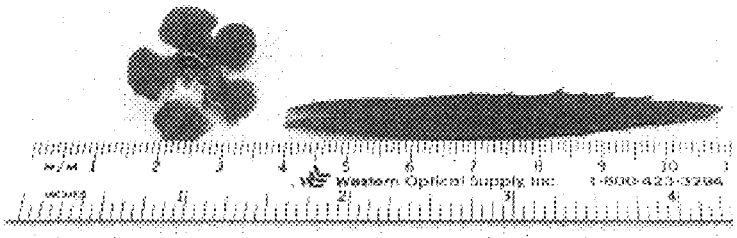
FIG. 2 illustrates a close-up view of individual flowers of 'Balangbeke'.

The chart used in the identification of colors described herein is the R.H.S. Colour Chart of The Royal Horticultural Society, London, England, 1995 edition, except where general color terms of ordinary significance are used. The color values were determined on May 14, 2003. The readings were taken between 1:00 and 3:00 p.m. under natural light conditions. The plants were produced from cuttings taken from stock plants and were grown in a double polycarbonate-covered greenhouse under conditions comparable to those used in commercial practice. The plants were grown in 10 cm pots for 10 weeks while utilizing a soilless growth medium. Greenhouse temperatures were maintained at approximately 65°–75° F. (18°–24° C.) during the day and approximately 50°–60° F. (10°–15° C.) during the night. Greenhouse light levels were maintained at approximately 4,000 to 7,000 footcandles during the day.

Botanical classification: *Angelonia augustifolia,* cultivar 'Balangbeke'.

Parentage:

*Female parent.*—Proprietary *Angelonia augustifolia* selection designated '190LV' (not patented).

*Male parent.*—Proprietary *Angelonia augustifolia* selection designated '225E' (not patented).

Propagation:

*Type cutting.*—Terminal stem.

*Time to initiate roots.*—Approximately 7 to 9 days.

*Time to develop roots.*—Approximately 21 to 28 days.

*Root description.*—Fine and fibrous.

*Rooting habit.*—Freely branching.

Plant description:

*Habit of growth.*—Moderately vigorous with good branching. At 10 weeks after the planting of a rooted cutting pinched at 3 weeks, an average of 15 flowering branches develop.

*Form.*—Upright and outwardly spreading.

*Size.*—A mature plant, 13 weeks after the planting of a rooted cutting, commonly measures approximately 32.1 cm in height from soil level to top of foliage and approximately 59.4 cm in diameter (area of spread).

*Branch.*—Shape: Square. Strength: Moderate. Length from soil level to base of raceme: Approximately 26 cm. Diameter: Approximately 2.6 mm. Texture: Sparsely glandular. Internode length at middle of branch: Approximately 3.8 cm. Color: 144B.

*Foliage.*—Type: Simple. Fragrance: None. Arrangement: Opposite. Orientation to stem: Acute. Shape: Elliptic. Margin: Serrate. Apex: Acute. Base: Decurrent. Length of leaf taken from middle of branch: Approximately 6.9 cm. Leaf width: Approximately 8 mm. Texture of upper and lower surfaces: Glabrous. Venation pattern: Pinnate. Color of upper and lower surfaces of young foliage: 144A with venation of N144A. Color of mature foliage: Upper surface: 137A with venation of N144A. Lower surface: 138A with venation of N144A.

Flowering description:

*Flowering habit.*—Freely flowering.

*Natural flowering season.*—Year round in greenhouse environment and spring through autumn in outdoor garden.

*Lastingness of individual bloom.*—Approximately 7 to 10 days.

*Inflorescence type/description.*—Axillary racemes. Length: 12.4 cm. Width: 4.8 cm. Number per plant: Approximately 15 open racemes per plant. Number of fully open flowers per raceme at any one time: Approximately 11.

Flower description:

*Type.*—Solitary, bi-labiate. Flowers have a slightly sweet fragrance and are persistent.

*Flower size/aspect.*—Length: Approximately 2.4 cm. Width: Approximately 2.1 cm. Depth: Approximately 7.6 mm. Aspect: Facing outward.

*Petals.*—Quantity: Five per flower, fused at base forming an upper lip having two lobes and a lower lip having three lobes.

*Upper lip.*—Lope apex: Obtuse. Lobe margin: Entire. Length of lobes: 7 mm. Width of lobes: 1.2 cm. Color of upper surface: Closest to N87B. Color of lower surface: N88C. Lobe texture: Densely glandular at margins. Gland color: Colorless, translucent.

*Lower lip.*—Lobe apex: Obtuse. Lobe margin: Entire. Length of lobes: 9 mm. Width of lobes: 1.1 cm. Color of upper surface of lateral lobes: Closest to N87C with spots of N79B. Color of lower surface of lateral lobes: N88C. Color of upper surface of central lobe: N87C. Color of lower surface of central lobe: Margin of N87B with 155C and spots of 187A in center and 145C at base. Texture: Densely glandular at margins. Gland color: Colorless, translucent.

*Pedicel.*—Length: Approximately 1.1 cm. Diameter: Approximately 1 mm. Angle to stem: Acute. Strength: Good. Texture: Glandular. Color: 146C.

*Bud.*—Shape: Ovoid. Diameter: Approximately 7 mm. Color: 157C.

*Sepals.*—Five, fused at base. Shape: Linear. Margin: Entire. Apex: Acute. Length: Approximately 3 mm. Width: Approximately 2 mm. Texture: Upper surface: Glabrous. Lower surface: Moderately glandular. Color: Both surfaces: 137C.

*Reproductive organs.*—Androecium: Stamen quantity: Four per flower. Stamen length: Approximately 3 mm. Filament color: 155B at base and middle, becoming N88D at anther. Anther length: 1 mm. Anther color: N88D. Amount of pollen: Moderate. Pollen color: 155D. Gynoecium: Pistil quantity: One per flower. Pistil length: 5 mm. Stigma length: Less than 1 mm. Stigma color: 155C. Style length: 3.5 mm. Style color: Lighter than 149D with streaks of N81B at base. Ovary diameter: 1 mm. Ovary color: 145B.

Seed and fruit production: Neither seed nor fruit production has been observed.

Disease and pest resistance: Resistance to pathogens and pests common to *Angelonia* has not been observed.

Hardiness zone: 'Balangbeke' is hardy in zones nine (9) and above.

What is claimed is:

1. A new and distinct cultivar of *Angelonia* plant named 'Balangbeke' substantially, as herein shown and described, which:

1. Exhibits purple-colored flowers,
2. Forms medium green-colored foliage, and
3. Exhibits a semi-prostrate to trailing, well branched growth habit.

* * * * *